(12) United States Patent
Fu et al.

(10) Patent No.: US 8,673,312 B2
(45) Date of Patent: Mar. 18, 2014

(54) **METHOD FOR ONE-STEP PURIFICATION OF RECOMBINANT *HELICOBACTER PYLORI* NEUTROPHIL-ACTIVATING PROTEIN**

(75) Inventors: Hua-Wen Fu, Hsinchu (TW); Kuo-Shun Shih, Hsinchu (TW); Chih-Chang Lin, Hsinchu (TW); Yu-Chi Yang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/560,593

(22) Filed: Jul. 27, 2012

(65) Prior Publication Data

US 2013/0190482 A1     Jul. 25, 2013

(30) Foreign Application Priority Data

Jan. 20, 2012   (TW) .............................. 101102406 A

(51) Int. Cl.
| | | |
|---|---|---|
| *A61K 39/38* | (2006.01) | |
| *A61K 35/00* | (2006.01) | |
| *A61K 48/00* | (2006.01) | |
| *C12P 9/00* | (2006.01) | |
| *C07C 7/12* | (2006.01) | |

(52) U.S. Cl.
USPC ..................... 424/184.1; 424/124; 424/234.1; 424/93.2; 435/42; 435/69.1; 435/71.1; 435/183; 585/800; 585/825

(58) Field of Classification Search
None
See application file for complete search history.

(56) References Cited

U.S. PATENT DOCUMENTS 7,038,012 B1    5/2006   Grandi

OTHER PUBLICATIONS

Kottakis et al. 2008 (FEBS Journal 275: 302-317).*
Wenzel et al. 2011 (Self-Inducible *Bacillus subtilis* expression system for reliable and inexpensive protein production by high-cell-density fermentation; Applied and Environmental Microbiology; 77(18):6419-6425).*
Kawamura F and Koi RH, Construction of a *Bacillus subtilis* double mutant deficient in extracellular alkaline and neutral proteases. J Bacteriol. 1984, 160: 442-444.
Tonello F., et al., The *Helicobacter pylori* neutrophil-activating protein is an iron-binding protein with dodecameric structure. Molecular Microbiology, 1999, 34: 238-246.
Wang Chung-An, et al., *Helicobacter pylori* neutrophil-activating protein promotes myeloperoxidase release from human neutrophils, Biochemical and Biophysical Research Communications, 2008, 377: 52-56.
Yeh, Chuan-Mei, et al., Improved electro-transformation protocol for *Bacillus subtilis* DB104, Taiwanese Journal of Agricultural Chemistry and Food Science, 2005, 43: 368-375.
Yeh, Chuan-Mei, et al., Enhancement of recombinant subtilisin YaB production by *Bacillus subtilis*, Food Biotechnology, 2007, 21: 105-117.
BIT's 1st Annual World Congress of Microbes—2011, in Beijing, China, "One-step chromatographic purification and functional characterization of recombinant *Helicobacter pylori* neutrophil-activating protein expressed in *Bacillus subtilis*", Jul. 30-Aug. 1, 2011.

* cited by examiner

*Primary Examiner* — Ja'Na Hines
*Assistant Examiner* — Mary Lyons
(74) *Attorney, Agent, or Firm* — WPAT, P.C.; Anthony King; Kay Yang

(57) ABSTRACT

*Helicobacter pylori* is closely associated with chronic gastritis, peptic ulcer disease, and gastric adenocarcinoma. *Helicobacter pylori* neutrophil-activating protein (HP-NAP), a virulence factor of *Helicobacter pylori*, plays an important role in pathogenesis of *Helicobacter pylori* infection. Since HP-NAP has been proposed as a candidate vaccine against *Helicobacter pylori* infection, an efficient way to obtain pure HP-NAP needs to be developed. In the present invention, recombinant HP-NAP expressed in *Bacillus subtilis* and *Escherichia coli* was purified through a single step of DEAE SEPHADEX ion-exchange chromatography with high purity. Also, purified recombinant HP-NAP was able to stimulate neutrophils to produce reactive oxygen species. Thus, recombinant HP-NAP obtained from our *Bacillus subtilis* expression system and *Escherichia coli* expression system is functionally active. Furthermore, this one-step negative purification method should provide an efficient way to purify recombinant HP-NAP expressed in *Bacillus subtilis* and *Escherichia coli* for basic studies, vaccine development, or drug design.

5 Claims, 16 Drawing Sheets

METHOD FOR ONE-STEP PURIFICATION OF RECOMBINANT *HELICOBACTER PYLORI* NEUTROPHIL-ACTIVATING PROTEIN

FIELD OF THE INVENTION

The present invention relates to a method for purification of a gene-transferred transformant by using an anion-exchange resin, particularly relates to a method for one-step purification of recombinant *Helicobacter pylori* neutrophil-activating protein.

BACKGROUND OF THE INVENTION

*Helicobacter pylori* (*H. pylori*) is a common gastric pathogen that causes gastritis, peptic ulcer disease, and gastric adenocarcinoma. *Helicobacter pylori* neutrophil-activating protein (HP-NAP) is a virulence factor of *H. pylori*. According to epidemiology reports in Taiwan, more than ten million people are infected with *H. pylori* among healthy population in Taiwan, and those people are also a high-risk group of suffering gastric adenocarcinoma. Therefore, infection of *H. pylori* becomes an important public health issue. Generally, drugs for treating *H. pylori* can be categorized into several groups, including: gastric acid suppressants, e.g. Proton Pump Inhibitors (PPIs) (e.g. Esomeprazole, Lansoprazole, Pantoprazole and Rabeprazole) and antibiotics (e.g. Amoxicillin and Clarithromycin).

*H. pylori* is closely associated with chronic gastritis, peptic ulcer disease, and gastric adenocarcinoma and lymphoma. HP-NAP, a virulence factor of *H. pylori*, plays an important role in pathogenesis of *H. pylori* infection. Since HP-NAP has been proposed as a candidate vaccine against *H. pylori* infection, an efficient way to obtain pure HP-NAP protein needs to be developed.

SUMMARY OF THE INVENTION

As described above, *Helicobacter pylori* (*H. pylori*) is closely associated with chronic gastritis, peptic ulcer disease, and gastric adenocarcinoma and lymphoma. *Helicobacter pylori* neutrophil-activating protein (HP-NAP) is a virulence factor of *H. pylori* and plays an important role in pathogenesis of *H. pylori* infection. Since HP-NAP has been proposed as a candidate vaccine against *H. pylori* infection, an efficient way to obtain pure HP-NAP protein needs to be developed.

The present invention relates to *Bacillus subtilis* (*B. subtilis*) expression system and *Escherichia coli* (*E. coli*) expression system that can express recombinant HP-NAP. Through a single step of negative purification using diethylaminoethyl (DEAE) SEPHADEX ion-exchange resin, recombinant HP-NAP expressed as the soluble protein can be simply purified with decreased endotoxin. Purified recombinant HP-NAP has a common α-helix structure and can stimulate neutrophils to produce reactive oxygen species (ROS). These results indicate that recombinant HP-NAP obtained from our *B. subtilis* expression system and *E. coli* expression system is correctly folded and functionally active. Furthermore, this one-step negative purification method using DEAE anion-exchange resins can provide an efficient way to purify recombinant HP-NAP expressed in *B. subtilis* and *E. coli* for basic studies, vaccine development, or drug design.

The present invention provides a method for one-step purification of recombinant *Helicobacter pylori* neutrophil-activating protein (HP-NAP). The method comprises the steps of: providing a sample containing recombinant HP-NAP, wherein the sample is obtained from a protein expression system that can express recombinant HP-NAP; purifying the sample by a diethylaminoethyl (DEAE) resin between a predetermined pH range; and collecting a unbound fraction and a wash fraction obtained through above step, wherein the unbound fraction and the wash fraction contain the recombinant HP-NAP having a predetermined purity.

Preferably, the method as mentioned above, wherein the predetermined pH range is between 7.5 and 9.0, further preferably is between 7.5 and 8.0.

Preferably, the method as mentioned above, wherein the recombinant HP-NAP is in a native form.

Preferably, the method as mentioned above, wherein the recombinant HP-NAP is a multimeric protein formed by α-helix monomers.

Preferably, the method as mentioned above, wherein the protein expression system is *B. subtilis* expression system or *E. coli* expression system.

Preferably, the method as mentioned above, wherein the DEAE resin is DEAE SEPHADEX resin.

Preferably, the method as mentioned above, wherein the DEAE resin is DEAE SEPHAROSE resin.

Preferably, the method as mentioned above, wherein the recombinant HP-NAP has a purity of at least 90%.

Preferably, the method as mentioned above further comprises condensing the unbound fraction and the wash fraction to increase purity, and filtering the unbound fraction and the wash fraction to remove endotoxin contained in the recombinant HP-NAP.

Preferably, the method as mentioned above, wherein the amount of endotoxin is less than 3.29 EU/mg of the recombinant HP-NAP after filtering.

In another embodiment of the present invention, the method as mentioned above further comprising exchanging the buffer of the unbound fraction and the wash fraction by dialysis, and filtering the unbound fraction and the wash fraction to remove endotoxin in recombinant HP-NAP.

Preferably, the method as mentioned above, wherein the amount of endotoxin is less than 2.22 EU/mg of the recombinant HP-NAP after filtering.

Through a single step of negative purification using DEAE SEPHADEX or DEAE SEPHAROSE ion-exchange resins, the recombinant HP-NAP expressed as the soluble protein can be simply purified with decreased endotoxin. Purified recombinant HP-NAP has a common α-helix structure and immunological activity.

The embodiments of the present invention are further described through below detailed examples and the drawings.

DETAILED DESCRIPTION

A method for one-step purification of recombinant *Helicobacter pylori* neutrophil-activating protein (HP-NAP) is described with reference to the preferred embodiments below, it is apparent to those skilled in the art that a variety of modifications and changes may be made without departing from the scope of the present invention which is intended to be defined by the appended claims.

The present invention provides a method for one-step purification of recombinant HP-NAP. The method comprises the steps of: providing a sample containing recombinant HP-NAP, wherein the sample is obtained from a protein expression system that can express recombinant HP-NAP; purifying the sample by a diethylaminoethyl (DEAE) resin between a predetermined pH range; and collecting a unbound fraction and a wash fraction obtained through above step, wherein the unbound fraction and the wash fraction contain the recombinant HP-NAP having a predetermined purity.

In the method as mentioned above, wherein the predetermined pH range is between 7.5 and 9.0. The recombinant HP-NAP is in a native form, and is a multimeric protein formed by α-helix monomers. The protein expression system is *B. subtilis* expression system or *E. coli* expression system.

The DEAE resin is DEAE SEPHADEX resin or DEAE SEPHAROSE resin. The recombinant HP-NAP has a purity of at least 90%. In addition, the method as mentioned above further comprises condensing the unbound fraction and the wash fraction to increase purity, and filtering the unbound fraction and the wash fraction to remove endotoxin contained in the recombinant HP-NAP, wherein the amount of endotoxin is less than 3.29 EU/mg of the recombinant HP-NAP after filtering. In another embodiment of the present invention, the method as mentioned above also further comprising exchanging the buffer of the unbound fraction and the wash fraction by dialysis, and filtering the unbound fraction and the wash fraction to remove endotoxin contained in the recombinant HP-NAP. Preferably, the method as mentioned above, wherein the amount of endotoxin is less than 2.22 EU/mg of the recombinant HP-NAP after filtering.

DEFINITION

The term "unbound fraction" as used herein, is preferably used in batch methods, also can be replaced by the term "flow-through fraction" in chromatographic methods.

Materials and Methods

Cloning of napA into *B. Subtilis* Expression System

Figure 1:
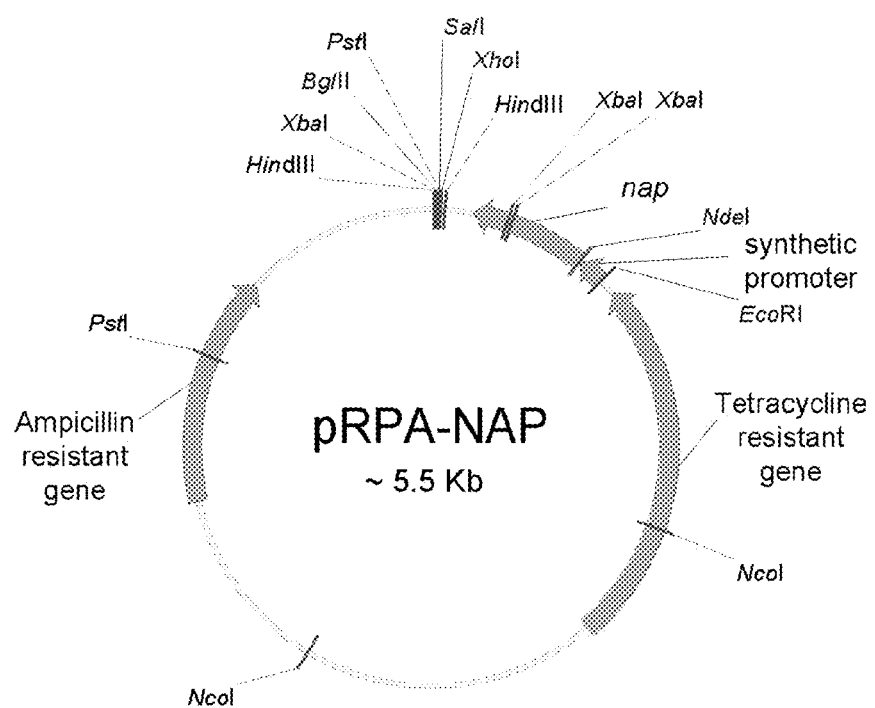
FIG. 1 exhibits the scheme of plasmid pRPA-NAP.

The napA gene was amplified by PCR from genomic DNA of *H. pylori* strain 26695 (accession no. AE000543, ATCC) and then cloned into pCR4-TOPO vector using the TOPO TA cloning kit (INVITROGEN, Carlsbad, Calif.) as previously described (Wang et al., 2008). The resulting plasmid, designated as pCR4-TOPO-NAP, was sequenced to confirm the correct insertion of napA. The DNA fragment containing napA was digested from pCR4-TOPO-NAP with Nde I and Hind III and then cloned into the pET28a expression vector (Novagen, Madison, Wis.). The resulting plasmid was designated as pET28a-His-NAP. The DNA fragment of napA was digested from pET28a-His-NAP with Nde I and Xho I and then cloned into the pRPA expression vector, a derivative vector of pEX5A (Yeh et al., 2007). The resulting plasmid was designated as pRPA-NAP. The map of pRPA-NAP is shown in FIG. 1.

The plasmid pRPA-NAP was transformed into a multiple-protease-deficient *B. subtilis* DB104 strain (Kawamura and Doi et al., 1984) by electroporation to express recombinant HP-NAP. The electro-transformation competent *B. subtilis* cells were prepared as previously described (Yeh et al., 2005). A volume of 100 µL, of *B. subtilis* DB104 electro-transformation competent cells were gently mixed with 1 µL of pRPA-NAP (0.34 ng) and then transferred into a prechilled electroporation cuvette with 2 mm gap (Molecular BioProducts, San Diego, Calif.). The cuvette was placed on ice for 5 min and electroporation of pRPA-NAP into *B. subtilis* DB104 was carried out at field strength of 8.75 kV/cm, capacitance of 25 nF, and resistance of 500Ω by Gene Pulser XCELL™ Electroporation System (BIORAD, Richmond, Calif.). The cells were then added in 1 mL of 2xLB recovery medium containing 3% tryptone, 1% yeast extract, 1% NaCl with shaking at 120 rpm at 37° C. for 2 hr. The transformed *B. subtilis* cells were selected by screening colonies on LB agar plates containing 10 µg/mL tetracycline.

Optimization of HP-NAP Expression in *B. subtilis*

The selected *B. subtilis* DB104 colony containing pRPA-NAP (*B. subtilis* DB104-pRPA-NAP) was grown in LB medium supplemented with 10 µg/mL tetracycline at 37° C. overnight with rotary shaking at 150 rpm. This overnight culture was then inoculated into LB medium supplemented with 10 µg/mL tetracycline in a volume ratio of 1% in several sterile flasks, and the resulting cultures were grown at 37° C. for 3 to 24 hr with rotary shaking at 180 rpm. The growth of the above cultures was measured in terms of absorption spectra at 600 nm by U-2800 UV-VIS spectrophotometer (Hitachi, Tokyo, Japan). In the meantime, the same cultures were harvested by centrifugation, and the cell pellets were resuspended in an equal culture volume of 20 mM Tris-HCl, pH 8.0, and 50 mM NaCl with 0.13 mM phenylmethylsulfonyl fluoride (PMSF), 10.67 µg/mL N-alpha-tosyl-L-lysinyl-chloromethylketone (TLCK), and 10.67 µg/mL N-tosyl-L-phenylalaninyl-chloromethylketone (TPCK). The bacterial suspensions were subsequently disrupted by ultrasonication and the cell lysates of *B. subtilis* were analyzed by 15% SDS-PAGE.

Large-Scale Expression of Recombinant HP-NAP in *B. subtilis*

The overnight culture of *B. subtilis* DB104-pRPA-NAP with absorbance of 2.0 to 2.1 at 600 nm was inoculated into LB medium with supplemented 10 μg/mL tetracycline in a volume ratio of 1%. The resulting culture was then grown at 37° C. with rotary shaking at 180 rpm until the absorbance at 600 nm reached 1.4 to 1.6. Afterwards, the cells were harvested by centrifugation at 6,000×g at 4° C. for 15 min. The cell pellets were subsequently stored frozen at −70° C. until purification.

Large-Scale Expression of Recombinant HP-NAP in *E. coli*

Expression of recombinant HP-NAP in *E. coli* was performed as previously described (Wang et al., 2008).

Lysis of *B. subtilis* and *E. coli*

The cell pellets of *B. subtilis* and *E. coli* were lysed by either ultrasonication or by high pressure homogenization. For ultrasonication, the bacterial suspensions were resuspended in an equal culture volume of indicated buffer and then disrupted by an ultrasonic processor SONICS VCX-750 (Sonics & Materials, Newtown, Conn.) on ice with 20% amplitude, independent ON and OFF pulse cycles of 1 second, and processing time of 5 min. For high pressure homogenization, the bacterial suspensions were resuspended in 1/10 culture volume of indicated buffer and then disrupted by a high pressure homogenizer (Avestin Inc., Ottawa, Canada) at 15,000 psi for 3 passes.

Optimization of purification of recombinant HP-NAP expressed in *B. subtilis* and *E. coli* by a batch method The cell pellets of either *B. subtilis* DB104-pRPA-NAP or *E. coli* BL21(DE3) cells harboring pET42a-NAP (Wang et al., 2008) obtained from large-scale expression of recombinant HP-NAP were resuspended in 20 mM Tris-HCl, pH 8.0, and 50 mM NaCl with 0.13 mM PMSF, 10.67 μg/mL TLCK, and 10.67 μg/mL TPCK. The bacterial suspension was disrupted by high pressure homogenization (Avestin Inc., Ottawa, Canada) and the cell lysates were centrifuged at 30,000×g at 4° C. for 1 hr. For experiment to optimize the buffer pH values, the supernatant was adjusted to pH 7.0, 7.5, 8.0, 8.5 and 9.0, and then was mixed with DEAE SEPHAROSE (Amersham Pharmacia Biotech, Sweden) and DEAE SEPHADEX A-25 (SIGMA ALDRICH, USA) resins, which were pre-equilibrated with the above Tris-buffer at the same pH as the cell lysate supernatants. For experiment to optimize the amount of proteins mixed with the resins, the supernatant was adjusted to the ratio of protein to resin ranging from 0.3 to 1.5 mg/mL with the above Tris-buffer at pH 8.0, and then was mixed with DEAE SEPHADEX A-25 resin. The above mixtures of the supernatant and resins were shaken on a rotator for 30 min at 4° C. to ensure complete protein adsorption to the resin. Then, the mixtures were centrifuged at 10,000×g at 4° C. for 30 seconds and the supernatants were collected as "unbound fractions". An equal resin volume of Tris-buffer at the same pH as the supernatants was added onto the resins for washing. The mixtures were shaken on a rotator at 4° C. for 10 min., and then were centrifuged as described above to collect the supernatants as "wash fractions". After five times for washing, an equal resin volume of elution buffer containing 20 mM Tris-HCl and 1 M NaCl at the same pH was added onto resins to elute proteins adsorbed on the resins. The mixtures were shaken on a rotator at 4° C. for 10 min, and then were centrifuged as described above to collect the supernatants as "bound fractions". This elution step was repeated twice. The fractions including unbound, wash, and bound fractions were analyzed by 15% SDS-PAGE or 10% native-PAGE.

Purification of Recombinant HP-NAP in *B. subtilis*

The cell pellets of *B. subtilis* DB104-pRPA-NAP obtained from large-scale expression of recombinant HP-NAP were resuspended in 20 mM Tris-HCl, pH 8.0, and 50 mM NaCl with 0.13 mM PMSF, 10.67 μg/mL TLCK, and 10.67 μg/mL TPCK. The bacterial suspension was disrupted by high pressure homogenizer and the cell lysate was centrifuged at 30,000×g at 4° C. for 1 hr. The supernatant was then loaded onto the XK 26/20 column (GE Healthcare Bio-Sciences, Sweden) prepacked with DEAE SEPHADEX A-25 resin, which was pre-equilibrated with 20 mM Tris-HCl, pH 8.0, and 50 mM NaCl, by using ÄKTAprime system (Amersham Pharmacia Biotech, Sweden). The flow rate was 1 mL/min and the column temperature was set at 4° C. The flow-through was collected in 3-mL fractions. The column was then washed with two column volumes (CVs) of 20 mM Tris-HCl, pH 8.0, and 50 mM NaCl at a flow rate of 5 mL/min. The volume of each collected fraction was 5 mL for the first CV and 10 mL for the second CV of the wash step. Finally, the proteins adsorbed on DEAE SEPHADEX resins were eluted with 2 CVs of 20 mM Tris-HCl, pH 8.0, and 1 M NaCl at the same flow rate and the eluate was collected in 10-mL fractions. The flow-through, wash, and elution fractions were analyzed by 15% SDS-PAGE. The flow-through fractions containing HP-NAP were then concentrated by using a stirred ultrafiltration cell (Aminco, model 8050) equipped with an Ultracel regenerated cellulose YM-30 membrane. During the concentration, the buffer was exchanged to Dulbecco's phosphate buffered saline (D-PBS), pH 7.2. HP-NAP was then filtered through an ACRODISC with Mustang E membrane (Pall, N.Y., USA) to eliminate the possible endotoxin contamination during the purification. The amount of endotoxin was less than 3.29 endotoxin unit (EU)/mg of HP-NAP. In addition to SDS-PAGE, purified recombinant HP-NAP was routinely subjected to gel filtration and native-PAGE analyses to confirm its multimeric properties.

Purification of Recombinant HP-NAP in *E. coli*

The cell pellets of *E. coli* BL21(DE3) cells harboring pET42a-NAP obtained from large-scale expression of recombinant HP-NAP were resuspended in 20 mM Tris-HCl, pH 8.0, and 50 mM NaCl with 0.13 mM PMSF, 10.67 μg/mL TLCK, and 10.67 μg/mL TPCK. The bacterial suspension was disrupted by high pressure homogenizer and the cell lysate was centrifuged at 30,000×g at 4° C. for 1 hr. The supernatant was mixed with DEAE SEPHADEX A-25 resin, which pre-equilibrated with 20 mM Tris-HCl, pH 8.0, and 50 mM NaCl. The mixture of supernatant and resin was shaken on a rotator at 4° C. for 1 hr. Then, the supernatant/resin slurry was transferred into an empty column and the flow-through was collected by gravity. The column was washed with five CVs of 20 mM Tris-HCl, pH 8.0, and 50 mM NaCl. Finally, the proteins adsorbed on DEAE SEPHADEX resins were eluted with 3 CVs of 20 mM Tris-HCl, pH 8.0, and 1 M NaCl. The volume of each collected fraction was 2 mL for the wash and elution steps. The flow-through, wash, and elution fractions were analyzed by 15% SDS-PAGE. The flow-through fraction containing HP-NAP was dialyzed against 1 L of D-PBS, pH 7.2, at 4° C. for 2 hr, and again dialyzed overnight with fresh D-PBS, using Spectra/Por dialysis tubing (Spectrum Laboratories, Rancho Dominguez, Calif., USA) with molecular weight cutoff at 12 to 14 kDa. HP-NAP was then filtered through an ACRODISC with Mustang E membrane (Pall, N.Y., USA) to eliminate the possible endotoxin contamination during the purification. The amount of endotoxin was less than 2.22 endotoxin unit (EU)/mg of HP-NAP. In addition to SDS-PAGE, purified recombinant HP-NAP was routinely subjected to gel filtration and native-PAGE analyses to confirm its multimeric properties.

Gel Filtration Analysis

A volume of 500 µL of the purified recombinant HP-NAP at 0.3 mg/mL was applied onto a HiLoad 16/60 SUPERDEX 200 prep grade column (GE Healthcare Bio-Sciences, Sweden), which was pre-equilibrated with D-PBS, pH 7.2, by using ÄKTA FPLC (Amersham Pharmacia Biotech, Sweden) and analyzed as previously described (Wang et al., 2008). A volume of 200 µL, of standard proteins for gel filtration (Bio-Rad Laboratories Inc., Hercules, Canada) was applied to the same column to evaluate the molecular weight of recombinant HP-NAP.

Analytical Ultracentrifugation

The sedimentation velocity experiment was performed on a Beckman Coulter ProteomeLab™ XL-I analytical ultracentrifuge equipped with UV absorbance optical detection system. Purified HP-NAP at a concentration of 0.3 mg/mL and D-PBS, pH 7.2, as a reference both in a volume of 500 µL were centrifuged at 135,556×g (41,000 rpm) and at a temperature of 20° C. using a 12-mm aluminum double-sector centerpiece in a four-hole An60 Ti analytical rotor equilibrated to 20° C. The UV absorbance data were collected at a wavelength of 280 nm in the radial increment of 0.003 cm with a single reading at each radius and at 3-min time intervals for each scan. The sedimentation coefficient distribution, $c(s)$, and the calculated molecular weight of HP-NAP were calculated by the software SEDFIT.

Circular Dichroism Spectroscopy

Recombinant HP-NAP, with a concentration of ~0.3 mg/mL, in D-PBS, pH 7.2, was subjected to circular dichroism (CD) analysis. The CD spectra were recorded on AVIV 62A DS spectrometer (AVIV Biomedical, Inc., Lakewood, N.J.) with a temperature controller at 25° C. using a 1 mm path-length cuvette. The CD data was obtained from the average value of at least two scans from 260 to 195 nm with 1 nm bandwidth at 0.5 nm intervals. A reference spectrum of D-PBS, pH 7.2 was also recorded. The CD spectrum of recombinant HP-NAP was calculated by subtracting the reference spectrum. The mean residue ellipticity (MRE) in the far UV was calculated with the formula: $MRE=\theta/(10 \times L \times C \times N)$, where the $\theta$, $L$, $C$, and $N$ are the measured signal in millidegrees, path-length of the cuvette, molar concentration of the protein, and number of peptide bond, respectively.

Isolation of Human Neutrophils

Human blood was collected from healthy volunteers under signed consent in accordance with the Declaration of Helsinki and approval from the Institutional Review Board of the National Tsing Hua University (NTHU), Hsinchu, Taiwan. A volume of 10 mL peripheral venous blood was drawn in vacuum blood collection tubes with sodium heparin. Heparinized blood was mixed with an equal volume of 3% dextran in 0.9% saline solutions and incubated at room temperature for 20 min to sediment erythrocytes. After dextran sedimentation, the leukocyte-rich plasma was centrifuged at 250×g at 5° C. for 10 min, and then the leukocyte suspension was layered onto Ficoll-Paque PLUS (GE Healthcare Bio-Sciences AS (Uppsala, Sweden)) followed by centrifugation at 400×g for 40 min at 20° C. with no brake. The pellet rich in polymorphonuclear cells was preserved and erythrocytes contaminated in the pellet were removed by hypotonic lysis. The cell pellet was then resuspended in 2 mL ice-cold D-PBS containing 5 mM D-glucose (D-PBS-G) and kept on ice until use within 5 hr. The final cell suspension, as judged by light microscopic examination at 400× magnification of at least 700 cells on Liu's stained cytocentrifuged slides, contained >90% neutrophils with a viability exceeding 92% as gauged by trypan blue exclusion test.

Oxidative Burst Assay

Isolated human neutrophils were resuspended at $2 \times 10^6$ cells/mL in D-PBS, pH 7.2, with 0.5 mM D-glucose (D-PBS-G). Aliquots of 50 µL of cell suspension were dispensed into individual wells of a 96-well black plate (Nunc, N.Y., USA) with a flat bottom and the cells were incubated at 37° C. Subsequently, 150 µL of the mixture containing 0.9 mM $CaCl_2$, 0.5 mM $MgCl_2$, 0.27 µM $H_2DCFH-DA$, and individual stimulus in the D-PBS (SIGMA ALDRICH, USA) was added into each well to a final volume of 200 mL. $H_2DCFH-DA$ and PMA were dissolved in methanol and DMSO at concentrations of 10 mM and 0.2 mM as the stock solutions, respectively. Both of them were diluted into D-PBS containing 0.9 mM $CaCl_2$ and 0.5 mM $MgCl_2$ immediately before use. The final concentrations of recombinant HP-NAP, PMA and $H_2DCFH-DA$ were 1, 0.08 µM and 0.2 µM, respectively. The fluorescence emission at 538 nm was monitored in triplicate every 30 min for 5 hr by a microplate fluorometer.

Miscellaneous Methods

Protein concentrations were routinely analyzed by the Bradford method using a commercial dye preparation (Bio-Rad, Hercules, Calif.), and bovine serum albumin (BSA) was used as a standard. The native-PAGE was performed similar to SDS-PAGE except that the protein samples were supplemented with non-denaturing sample buffer containing 62.5 mM Tris-HCl, pH 6.8, 10% glycerol, and 0.01% bromophenol blue and that electrophoresis was performed at 4° C. using Tris-glycine system without SDS. The amount of endotoxin was determined by Super Laboratory Company (Taipei, Taiwan) using enzyme-linked immunosorbent assay (ELISA) with the detection limit of 0.005 to 2 EU/mL.

Statistical Analysis

The percentage purity of HP-NAP was calculated from the intensity of protein bands on SDS-PAGE as follows: purity (%)=(intensity of HP-NAP)/(intensity of HP-NAP+ intensities of impurity)×100. The intensity of protein bands was quantified by densitometry analysis using multi gauge software V3.0 (Fujifilm, Japan). Data are represented as the mean±standard deviation (S.D.). Statistical analyses were performed by using Excel 2010 software (Microsoft). The statistical significance was determined by Student's t-test. A probability (p) value of less than 0.05 was considered to represent statistical significance.

Embodiment 1

Expression of Recombinant HP-NAP in *B. subtilis* and *E. coli*

Figure 2:
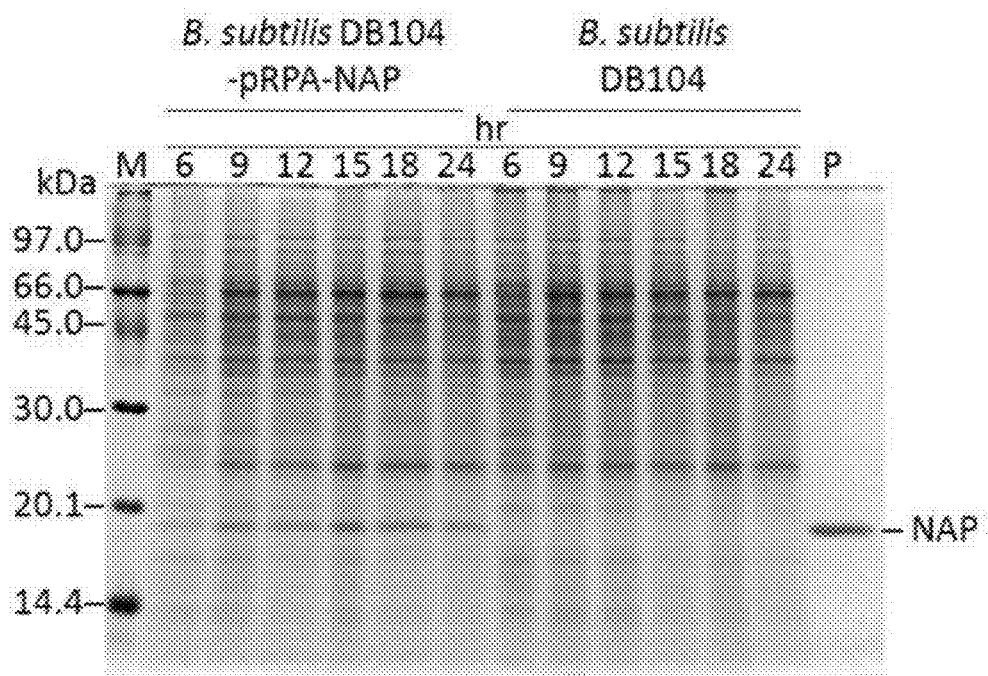
FIG. 2 exhibits the expression of recombinant HP-NAP in *B. subtilis*.
Figure 3:
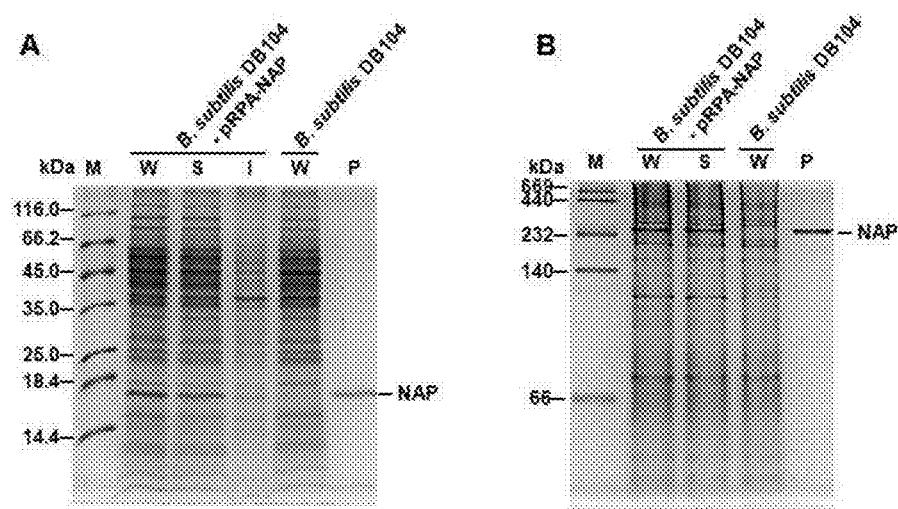
FIGS. 3A-3B exhibit recombinant HP-NAP expressed as a soluble multimeric protein from *B. subtilis*; 3A: soluble protein, 3B: multimeric protein.

To avoid the lipopolysaccharide (LPS) contamination, we employed the *B. subtilis* DB 104 expression system to express HP-NAP. The nap gene was cloned into pRPA expression vector, and then transformed into *B. subtilis* DB104 for protein expression (FIG. 1). Since the induction procedure is not required for protein expression in this *B. subtilis* expression system, it is important to determine the optimal culture time to achieve the maximal expression of recombinant HP-NAP. Here, we first monitored the growth of *B. subtilis* DB104 with or without harboring pRPA-NAP. It took 12 hr for *B. subtilis* DB104 harboring pRPA-NAP to reach the stationary phase and only 9 hr for *B. subtilis* DB104 (data not shown). The amount of recombinant HP-NAP expressed in *B. subtilis* at each culture time was further analyzed by SDS-PAGE. At all culture time points, the protein with a molecular weight of approximate 17 kDa corresponding to recombinant HP-NAP was expressed in *B. subtilis* harboring pRPA-NAP (FIG. 2). The maximum level of HP-NAP expression was achieved around 15 hr incubation (FIG. 2). No expression of HP-NAP was observed in *B. subtilis* DB104 (FIG. 2). Furthermore, the recombinant HP-NAP expressed in *B. subtilis* was mainly present in the soluble fraction of the cell lysate as analyzed by SDS-PAGE (FIG. 3A). Native-PAGE analysis of the soluble fraction of the cell lysate showed that a major protein with apparent molecular weight of a little bit over 232 kDa corresponding to recombinant HP-NAP was present in *B. subtilis* harboring pRPA-NAP but not in the *B. subtilis* DB104 (FIG. 3B). These results indicate that the recombinant HP-NAP expressed in *B. subtilis* as a soluble multimeric protein.

In addition, the expression of recombinant HP-NAP in *E. coli* is shown in previous report (Wang et al. 2008).

Embodiment 2

Figure 4:
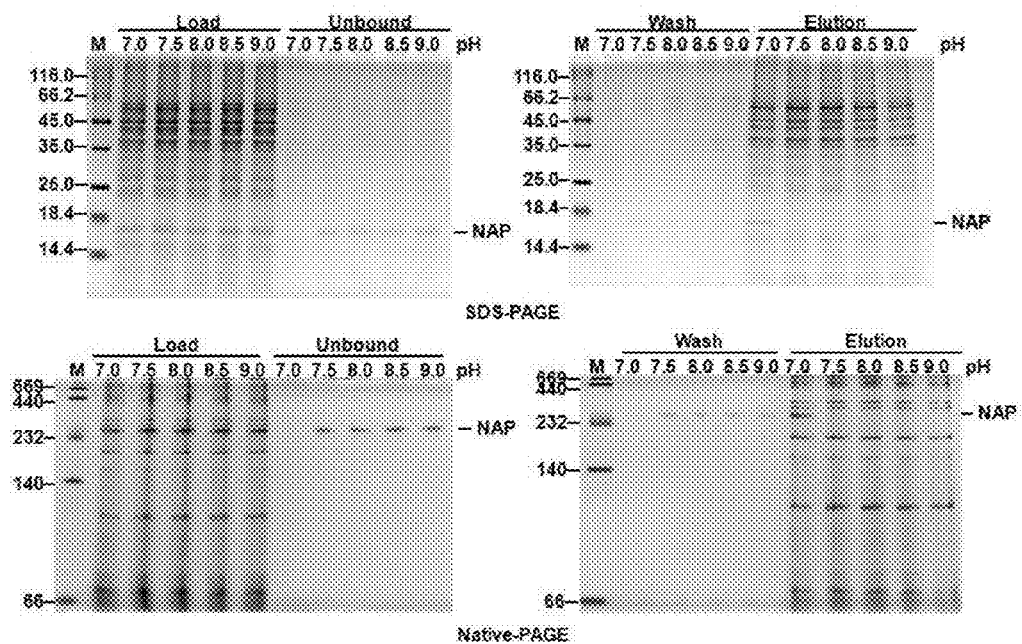
FIG. 4 exhibits small-scale batch method to optimize the pH to purify HP-NAP expressed in *B. subtilis* by DEAE SEPHADEX resin.
Figure 5:
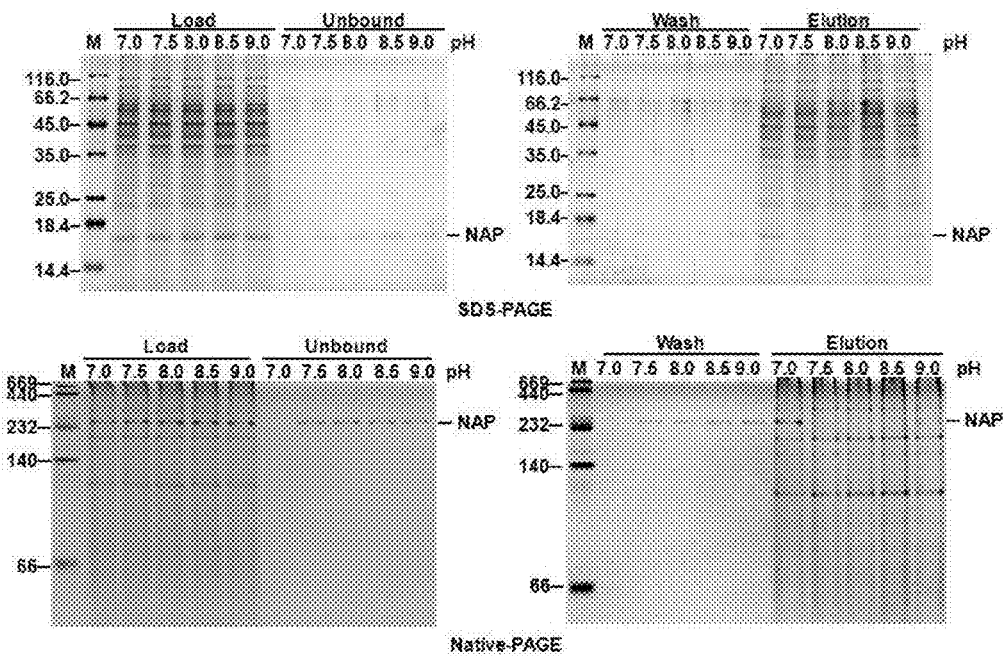
FIG. 5 exhibits small-scale batch method to optimize the pH to purify HP-NAP expressed in *B. subtilis* by DEAE SEPHAROSE resin.

Purification of Recombinant HP-NAP Expressed in *B. Subtilis* by One-Step DEAE Anion-Exchange Chromatography Due to the large molecular size of HP-NAP, gel filtration has been applied to purify recombinant HP-NAP expressed in *E. coli* (Wang et al., 2008). However, it is time-consuming and more than one chromatographic method is needed for purifying HP-NAP with high purity. In addition, several protein bands originated from *B. subtilis* with the molecular weight between 140 kDa and 232 kDa were detected in the soluble fraction of *B. subtilis* expressing HP-NAP analyzed by native-PAGE (FIG. 3B). It might be difficult to separate the recombinant HP-NAP from these proteins by applying gel filtration. Since the isoelectric point (pI) of HP-NAP was reported to be 6.75 (Tonello et al., 1999), we chose DEAE anion-exchange chromatography to purify recombinant HP-NAP expressed in *B. subtilis* using the buffer with pH value higher than 6.75. To optimize the purification condition, five different buffer pH values, 7.0, 7.5, 8.0, 8.5, and 9.0, in combination with either DEAE SEPHADEX or DEAE SEPHAROSE resins were tested for their feasibility to purify recombinant HP-NAP in *B. subtilis* by using a small-scale batch method. At pH 7.5 to 9.0, recombinant HP-NAP was mainly present in the unbound fractions and reached a high degree of purity using DEAE SEPHADEX (FIG. 4) and DEAE SEPHAROSE (FIG. 5) resins. Under the same conditions, recombinant HP-NAP was also found in the wash fractions by native-PAGE analysis (FIGS. 4 and 5). At pH 7.0, majority of recombinant HP-NAP was detected in the bound fractions for both resins (FIGS. 4 and 5). However, most of the proteins originated from *B. subtilis* were present in the bound fractions for both resins regardless of the pH values investigated (FIGS. 4 and 5). Under all five pH values, recombinant HP-NAP kept its multimeric structure (FIGS. 4 and 5). This finding raises the possibility that the recombinant HP-NAP might be able to be purified from the unbound fraction rather than the bound fraction, as traditionally applied for ion-exchange chromatography. When the purities of the recombinant HP-NAP in the unbound fractions of the two resins were compared, DEAE SEPHADEX resins showed better performance than DEAE SEPHAROSE resins in purification of recombinant HP-NAP at pH 7.5 to 9.0 (FIGS. 4 and 5). Thus, negative chromatography could be applied to isolate highly pure recombinant HP-NAP from *B. subtilis* through the collection of the unbound fractions using DEAE SEPHADEX resins at pH 7.5 to 9.0.

Figure 6:
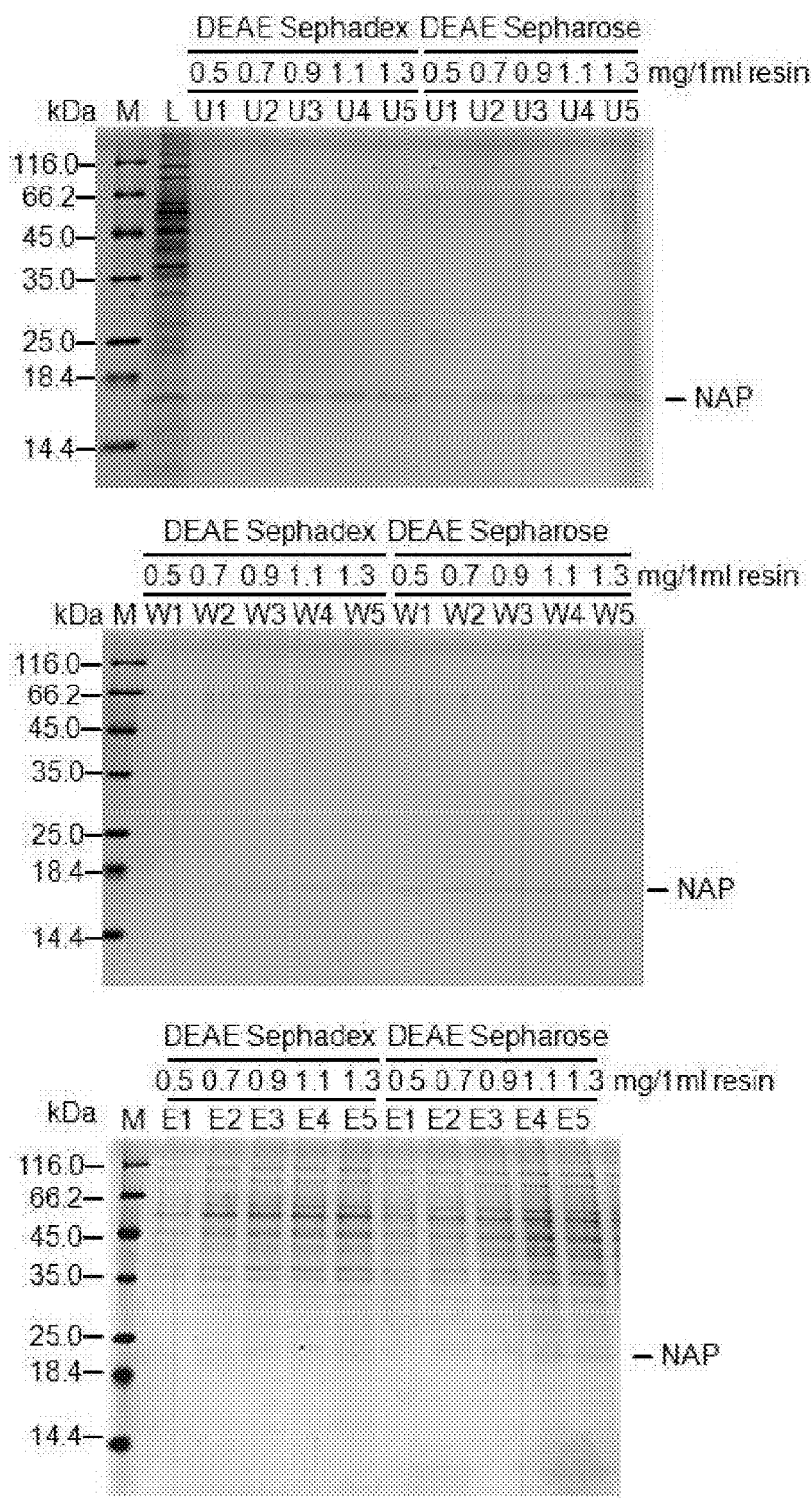
FIG. 6 exhibits small-scale batch method to optimize the amount of protein from *B. subtilis* to be loaded on DEAE SEPHADEX and SEPHAROSE resins for purification of HP-NAP at pH 8.

To develop a strategy by using negative chromatography to purify recombinant HP-NAP expressed in *B. subtilis* in one step, we then applied the small-scale batch method to determine the optimal amount of proteins from whole cell lysate of *B. subtilis* DB 104-pRPA-NAP to be loaded onto DEAE SEPHADEX and DEAE SEPHAROSE resins at pH 8.0 to obtain a maximum amount of highly pure recombinant HP-NAP. In this experiment, the ratio ranging from 0.5 to 1.3 of mg proteins from whole cell lysates per milliliter of DEAE SEPHADEX and DEAE SEPHAROSE resins were used to examine whether most of the proteins originated from *B. subtilis* were bound to the resins. As expected, the recombinant HP-NAP was still remained in the unbound fractions under these conditions (FIG. 6). However, the endogenous proteins from *B. subtilis* were gradually increased in the wash fractions when the ratio of protein to resin increased to 0.9 to 1.3 mg/mL (FIG. 6). Even though most of the endogenous proteins from *B. subtilis* were present in the bound fractions, the binding of these proteins to the resins had achieved the maximum level with the ratio of protein to resin ranging from 0.7 to 1.3 mg/mL (FIG. 6). These results indicated that the optimal loading ratio of the amount of proteins from whole cell lysates to the volume of DEAE SEPHADEX and DEAE SEPHAROSE resins should be below 0.7 mg/mL at pH 8.0.

In conclusion, the amount of protein to be loaded on to DEAE SEPHADEX resins to purify HP-NAP from *B. subtilis* should be less than 0.7 mg protein/mL resins, and the amount of protein to be loaded on to DEAE SEPHAROSE resins to purify HP-NAP from *B. subtilis* should be less than 0.7 mg protein/mL resins to achieve the highest purity.

Figure 7:
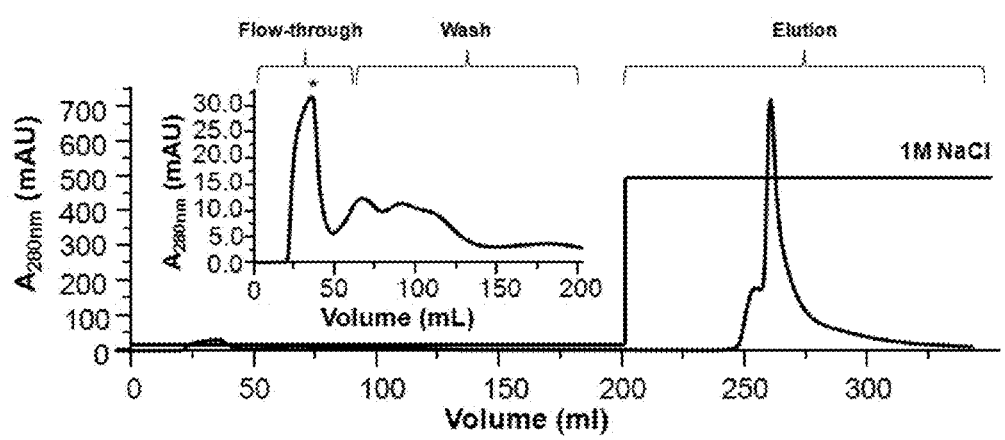
FIG. 7 exhibits the chromatogram of large-scale purification of HP-NAP expressed in *B. subtilis* by DEAE SEPHADEX ion exchange column.

We then applied this negative chromatography approach to purify the recombinant HP-NAP expressed in *B. subtilis* using DEAE SEPHADEX column at pH 8.0 by keeping the ratio of protein to resin below 0.7 mg/mL. As expected, recombinant HP-NAP was present in the flow-through fractions (FIG. 7, asterisk of the inset). Most of the endogenous proteins from *B. subtilis* were bound to DEAE SEPHADEX resins and then eluted under the high salt condition (FIG. 7). After the flow-through fractions containing recombinant HP-NAP were concentrated, coupled with a simultaneous buffer exchange using ultrafiltration membrane with a higher-molecular-weight cutoff, the purity of recombinant HP-NAP was further increased (FIG. 8A). The purified HP-NAP was expressed as a multimeric protein with molecular weight of around 232 kDa by native-PAGE analysis (FIG. 8B). The details of a typical purification of recombinant HP-NAP from *B. subtilis* are summarized in Table 1. Since the purity of recombinant HP-NAP was greatly elevated to 94.33% after the step of ion-exchange chromatography using DEAE SEPHADEX resins, by which a 16-fold purification with a 63% recovery was achieved, supporting that such negative chromatography approach was an efficient step in the purification procedure. Concentration and buffer exchange did not affect the yield of recombinant HP-NAP, whereas removal of endotoxin reduced the overall yield of ~5.8% (Table 1). The final yield of the pure recombinant HP-NAP was ranging from 1.3 mg to 1.5 mg per gram of *B. subtilis* cell paste. The overall purity of HP-NAP was higher than 92% in the preparations using this purification procedure. Thus, recombinant HP-NAP can be efficiently purified from *B. subtilis* by one-step negative chromatography using DEAE SEPHADEX anion-exchange resins.

TABLE 1

Purification summary table of recombinant HP-NAP from *B. subtilis*[a]

| Purification step | Amount of protein (mg)[b] | Volume (mL) | Purity (%)[c] | Estimated amount of HP-NAP (mg)[d] | Recovery of HP-NAP (%)[e] |
|---|---|---|---|---|---|
| Whole cell lysate | 45.09 | 27 | 4.94 | 2.23 | 100 |
| Supernatant | 38.07 | 27 | 5.64 | 2.15 | 96.41 |

TABLE 1-continued

Purification summary table of recombinant HP-NAP from *B. subtilis*[a]

| Purification step | Amount of protein (mg)[b] | Volume (mL) | Purity (%)[c] | Estimated amount of HP-NAP (mg)[d] | Recovery of HP-NAP (%)[e] |
|---|---|---|---|---|---|
| DEAE SEPHADEX chromatography | 1.44 | 36 | 94.33 | 1.36 | 60.99 |
| Stirred ultrafiltration | 1.44 | 4.8 | 95.38 | 1.37 | 61.43 |
| ACRODISC syringe filtration | 1.3 | 4.65 | 95.37 | 1.24 | 55.61 |

[a]0.84 g of *B. subtilis* cell paste from 300 mL culture.
[b]Values determined by Bradford method with BSA as the reference.
[c]Values determined from densitometry measurement by using multi gauge V3.0 software.
[d]Values determined by multiplying the values in "Amount of protein" and "Purity" columns
[e]Values determined by dividing the estimated amount of HP-NAP from each purification step by that of whole cell lysate.

In conclusion, using DEAE SEPHADEX resins, HP-NAP can be purified from *B. subtilis* at pH 7.5 to 9.0 by collection of the unbound fraction and the wash fraction in one-step with purity higher than 90%. Additionally, using DEAE SEPHAROSE resins, HP-NAP can be purified from *B. subtilis* at pH 7.5 to 9.0 by collection of the unbound fraction and/or the wash fraction in one-step with the similar purity.

Embodiment 3

Figure 9:
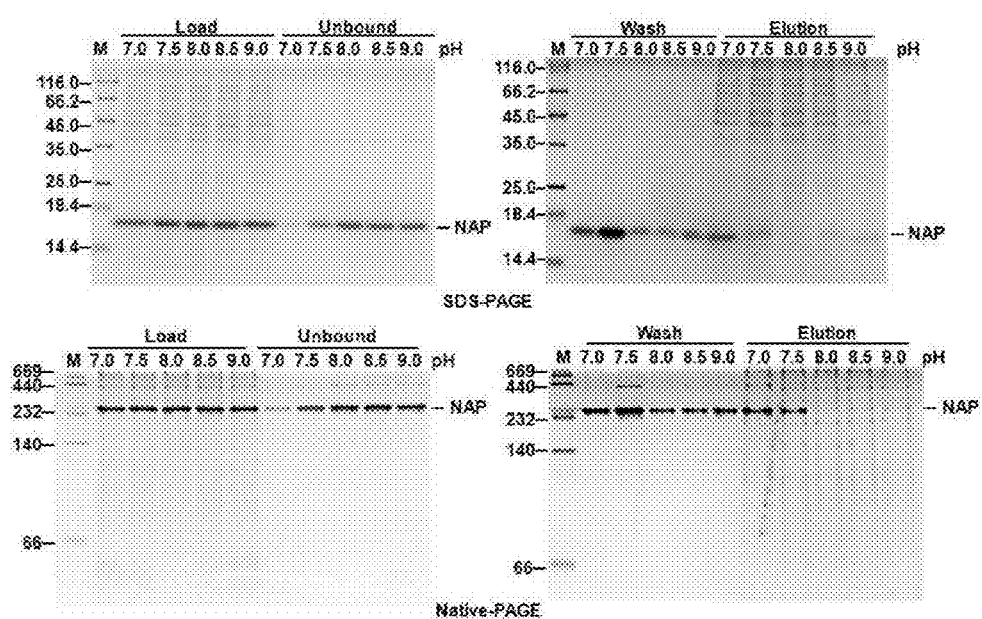
FIG. 9 exhibits small-scale batch method to optimize the pH to purify HP-NAP expressed in *E. coli* by DEAE SEPHADEX resin.
Figure 10:
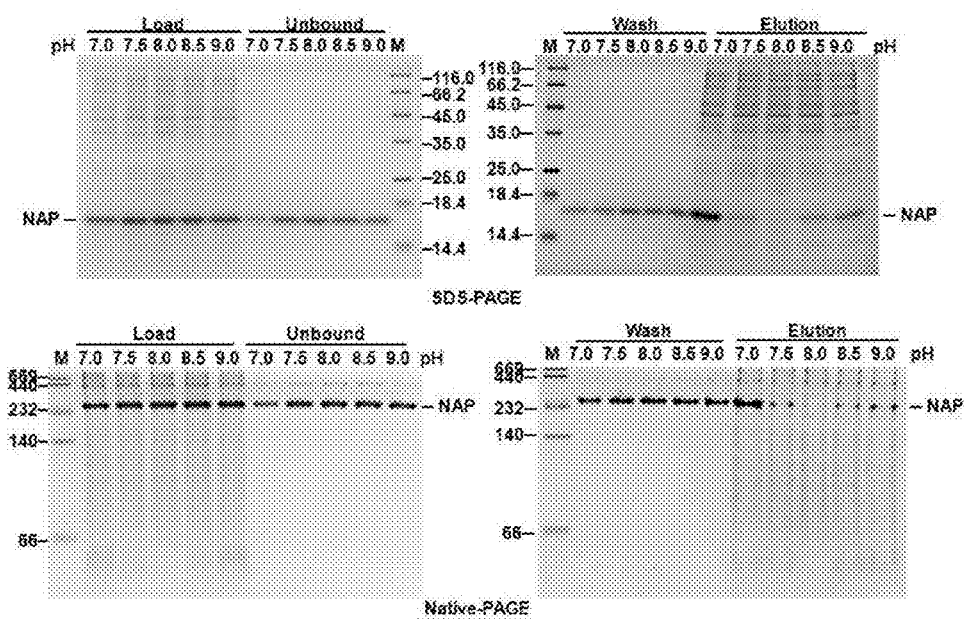
FIG. 10 exhibits small-scale batch method to optimize the pH to purify HP-NAP expressed in *E. coli* by DEAE SEPHAROSE resin.

Purification of Recombinant HP-NAP Expressed in *E. coli* by One-Step DEAE Anion-Exchange Chromatography In addition to purify recombinant HP-NAP expressed in *B. subtilis* by this one-step negative chromatography using DEAE SEPHADEX anion-exchange resins, the similar approach was applied to purify recombinant HP-NAP expressed in *E. coli*. To optimize the purification condition, five different buffer pH values, 7.0, 7.5, 8.0, 8.5 and 9.0 in combination with either DEAE SEPHADEX or DEAE SEPHAROSE resins were tested for their feasibility to purify recombinant HP-NAP in *E. coli* by using a small-scale batch method. At pH 7.5 to 9.0, recombinant HP-NAP was mainly present in the unbound and wash fractions, and reached a high degree of purity using DEAE SEPHADEX (FIG. 9) or DEAE SEPHAROSE (FIG. 10) resins. At pH 7.0, majority of recombinant HP-NAP was detected in the bound fractions for both resins (FIGS. 9 and 10). However, most of the proteins originated from *E. coli* were present in the bound fractions for both resins regardless of the pH values investigated (FIGS. 9 and 10). Under all five pH values, recombinant HP-NAP kept its multimeric structure. (FIGS. 9 and 10). These findings are consistent with the findings in the Embodiment 2, in which *B. subtilis* expression system was used to express HP-NAP. Thus, the recombinant HP-NAP expressed in *E. coli* should be able to be purified from the unbound and wash fractions rather than the bound fraction. When the purities of the recombinant HP-NAP in the unbound and wash fractions isolated by the two resins were compared, DEAE SEPHAROSE resins showed better performance than DEAE SEPHADEX resins in purification of recombinant HP-NAP at pH 7.5 to 9.0. However, for both resins, the purity is higher than 90% through the collection of the unbound and wash fractions.

Figure 11:
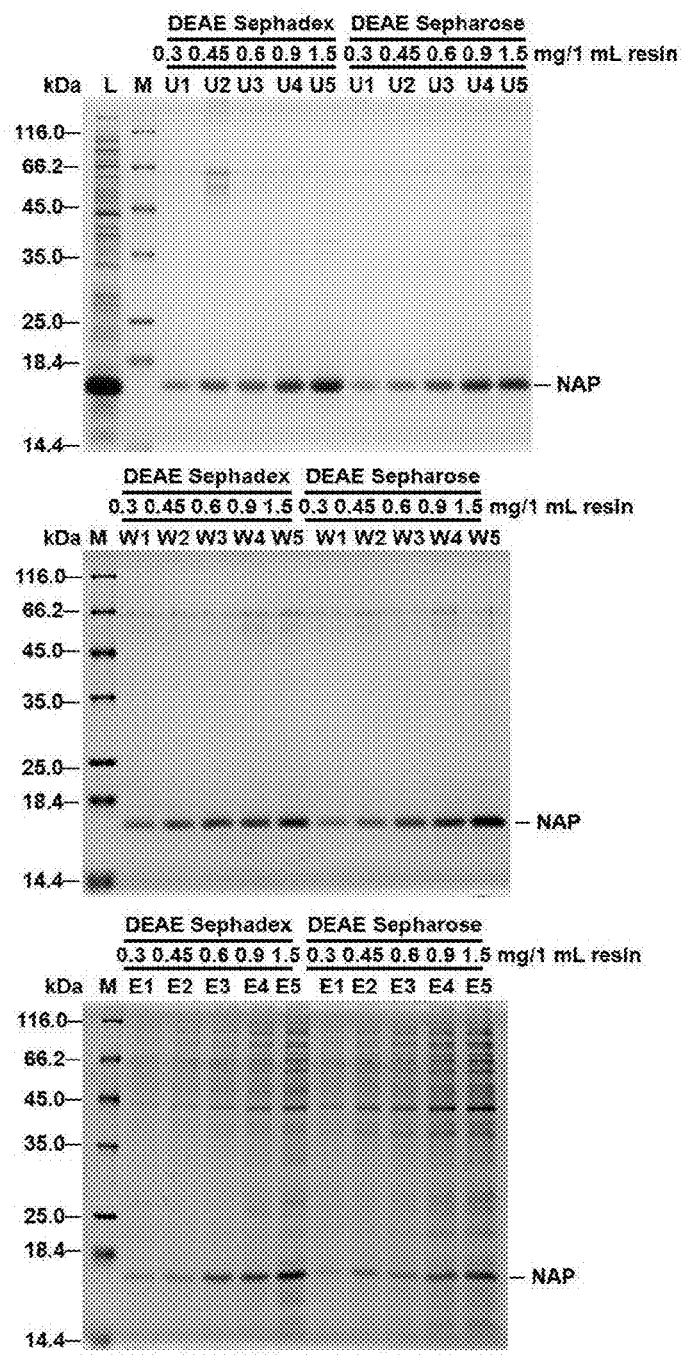
FIG. 11 exhibits small-scale batch method to optimize the amount of protein from *E. coli* to be loaded on DEAE SEPHADEX and SEPHAROSE resins for purification of HP-NAP at pH 8.

To develop a strategy by using negative chromatography to purify recombinant HP-NAP expressed in *E. coli* in one step, we then applied the small-scale batch method to determine the optimal amount of proteins from whole cell lysate of *E. coli* to be loaded onto DEAE SEPHADEX and SEPHAROSE resins at pH 8.0 to obtain a maximum amount of highly pure recombinant HP-NAP. In this experiment, the ratio ranging from 0.3 to 1.5 mg proteins from whole cell lysates per milliliter of DEAE SEPHADEX and SEPHAROSE resins were used to examine whether most of the proteins originated from *E. coli* were bound to the resins. As expected, the recombinant HP-NAP was still remained in the unbound fractions under these conditions (FIG. 11). Even though both recombinant HP-NAP and the endogenous proteins from *E. coli* were gradually increased in the bound fractions when the ratio of protein to resin increased to 0.3 to 1.5 mg/mL, most of recombinant HP-NAP was present in the unbound and wash fractions with purity higher than 90% (FIG. 11). These results indicated that the optimal loading ratio of the amount of proteins from whole cell lysates to the volume of DEAE SEPHADEX and SEPHAROSE resins could achieve up to 1.5 mg/mL at pH 8.0.

Figure 12:
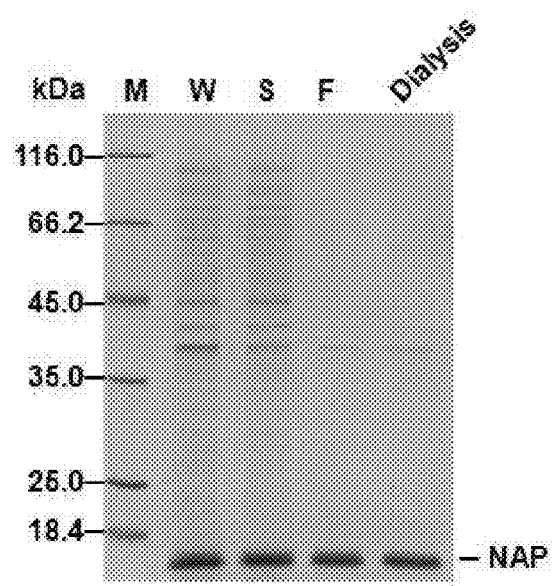
FIGS. 12A-12B exhibit purified HP-NAP expressed in *E. coli* by DEAE SEPHADEX ion exchange resins; 12A: soluble protein, 12B: multimeric protein.
Figure 12:
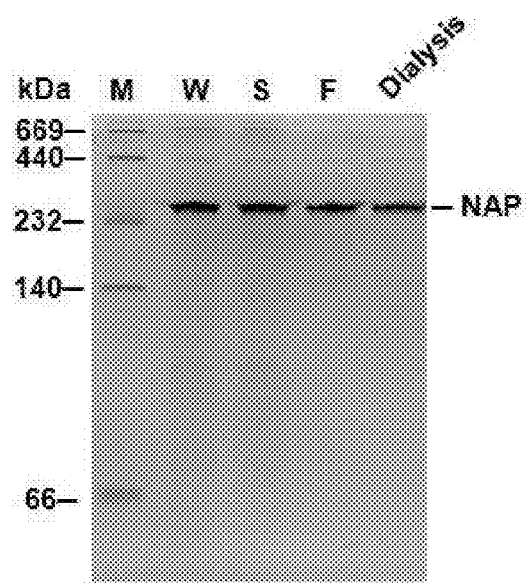

We then applied this negative purification approach to purify the recombinant HP-NAP expressed in *E. coli* using DEAE SEPHADEX resins at pH 8.0 by keeping the ratio of protein to resin at 1.5 mg/mL by batch method. As expected, recombinant HP-NAP was present in the flow-through fractions (FIG. 12A). The purified HP-NAP was expressed as a multimeric protein with molecular weight of around 232 kDa by native-PAGE analysis (FIG. 12B). Since the concentration of recombinant HP-NAP in the flow-through fraction is high enough, the flow-through fraction was subjected to dialysis for buffer exchange. The details of a typical purification of recombinant HP-NAP from *E. coli* are summarized in Table 2. Since the purity of recombinant HP-NAP was greatly elevated to 91.73% after the step of ion-exchange chromatography using DEAE SEPHADEX resin, by which a 1.3-fold purification with a 90% recovery was achieved, supporting that such negative purification approach was an efficient step in the purification procedure. Dialysis for buffer-exchange did not affect the yield of recombinant HP-NAP, whereas removal of endotoxin reduced the overall yield of ~1.4% (Table 2). The final yield of the pure recombinant HP-NAP was 177 mg per gram of *E. coli* cell paste and the purity of HP-NAP was ~91%. Thus, recombinant HP-NAP can be efficiently purified from *E. coli* by one-step negative purification using DEAE SEPHADEX anion-exchange resin by batch method.

TABLE 2

Purification summary table of recombinant HP-NAP from *E. coli*[a]

| Purification step | Amount of protein (mg)[b] | Volume (mL) | Purity (%)[c] | Estimated amount of HP-NAP (mg)[d] | Recovery of HP-NAP (%)[e] |
|---|---|---|---|---|---|
| Whole cell lysate | 3.75 | 6.7 | 70.4 | 2.64 | 100 |
| Supernatant | 3.38 | 6.7 | 75.3 | 2.54 | 96.2 |
| DEAE SEPHADEX chromatography | 2.68 | 6.3 | 90.12 | 2.42 | 91.2 |
| Dialysis | 2.70 | 6.1 | 90.18 | 2.43 | 91.9 |
| ACRODISC syringe filtration | 2.60 | 5.8 | 91.73 | 2.39 | 90.5 |

[a]0.0135 g of *E. coli* cell paste from 100 mL culture.
[b]Values determined by Bradford method with BSA as the reference.
[c]Values determined from densitometry measurement by using multi gauge V3.0 software.
[d]Values determined by multiplying the values in "Amount of protein" and "Purity" columns
[e]Values determined by dividing the estimated amount of HP-NAP from each purification step by that of whole cell lysate.

In conclusion, using either DEAE SEPHADEX or SEPHAROSE resins, HP-NAP can be purified from *E. coli* at pH 7.5 to 9.0 by collection of unbound fractions and wash fraction in one-step with purity higher than 90%.

Embodiment 4

Figure 13:
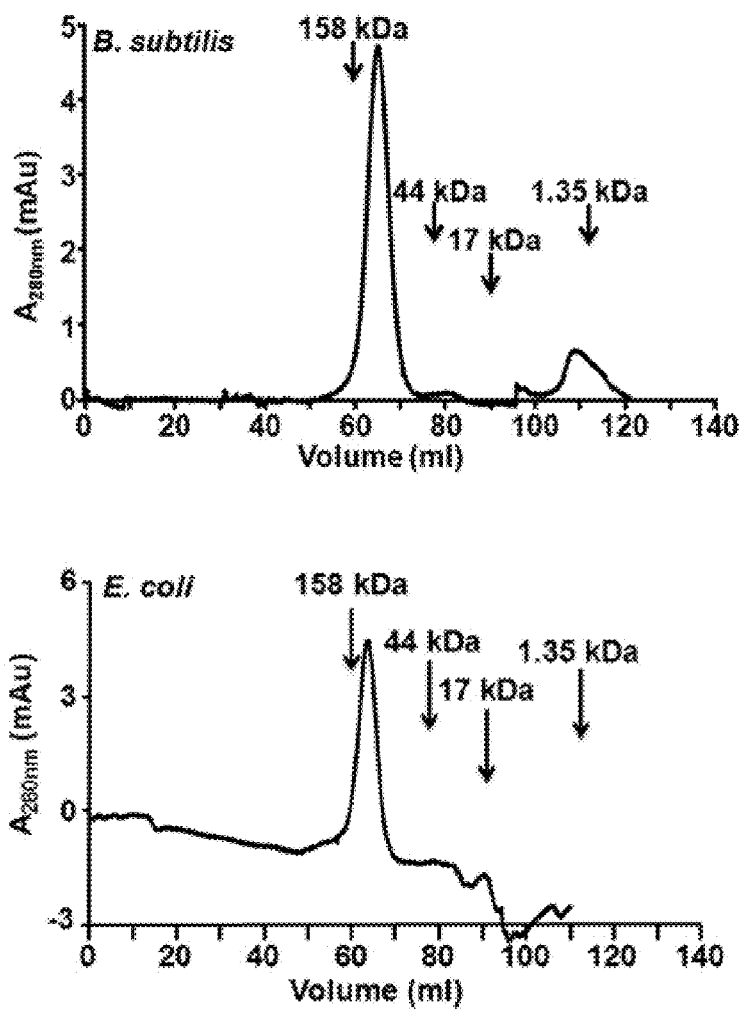
FIGS. 13 and 14 exhibit the physical analysis of purified HP-NAP expressed in *B. subtilis* and *E. coli* by DEAE SEPHADEX ion exchange resins for its multimeric property.
Figure 14:
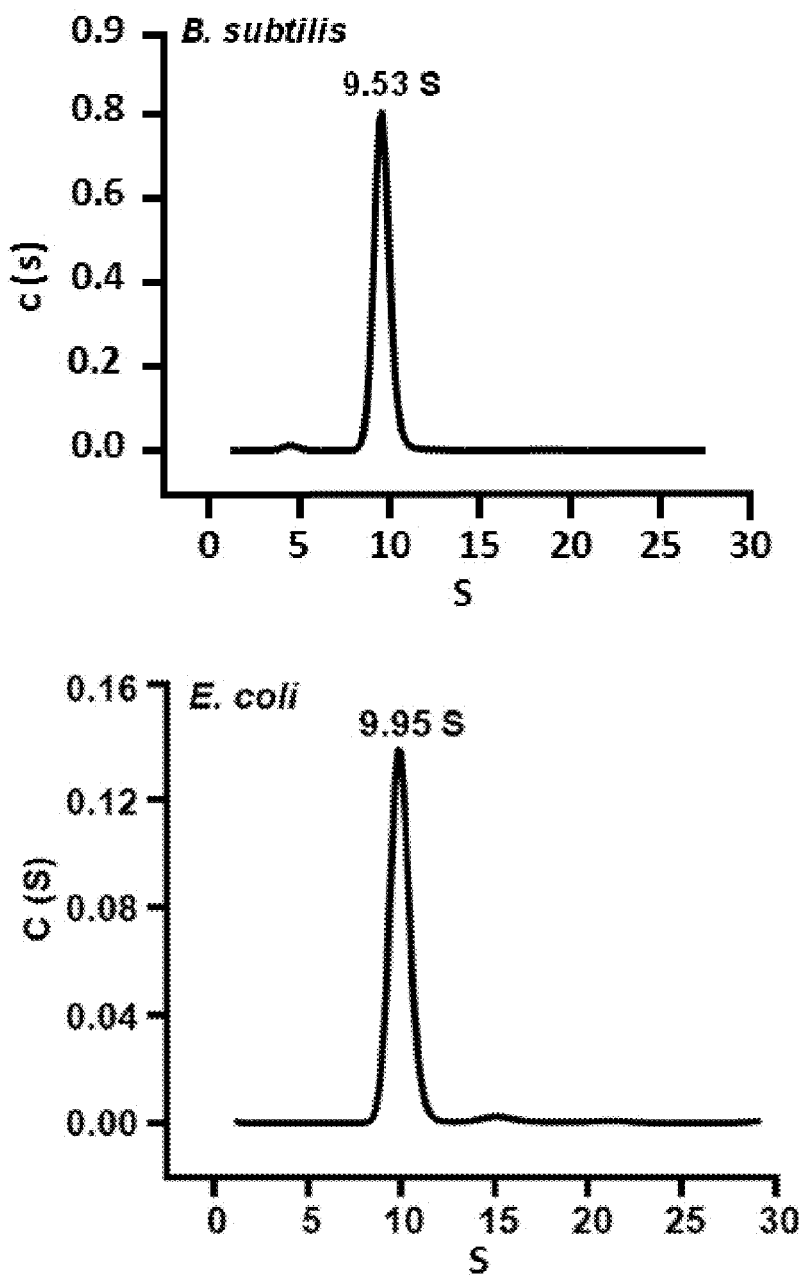
Figure 15:
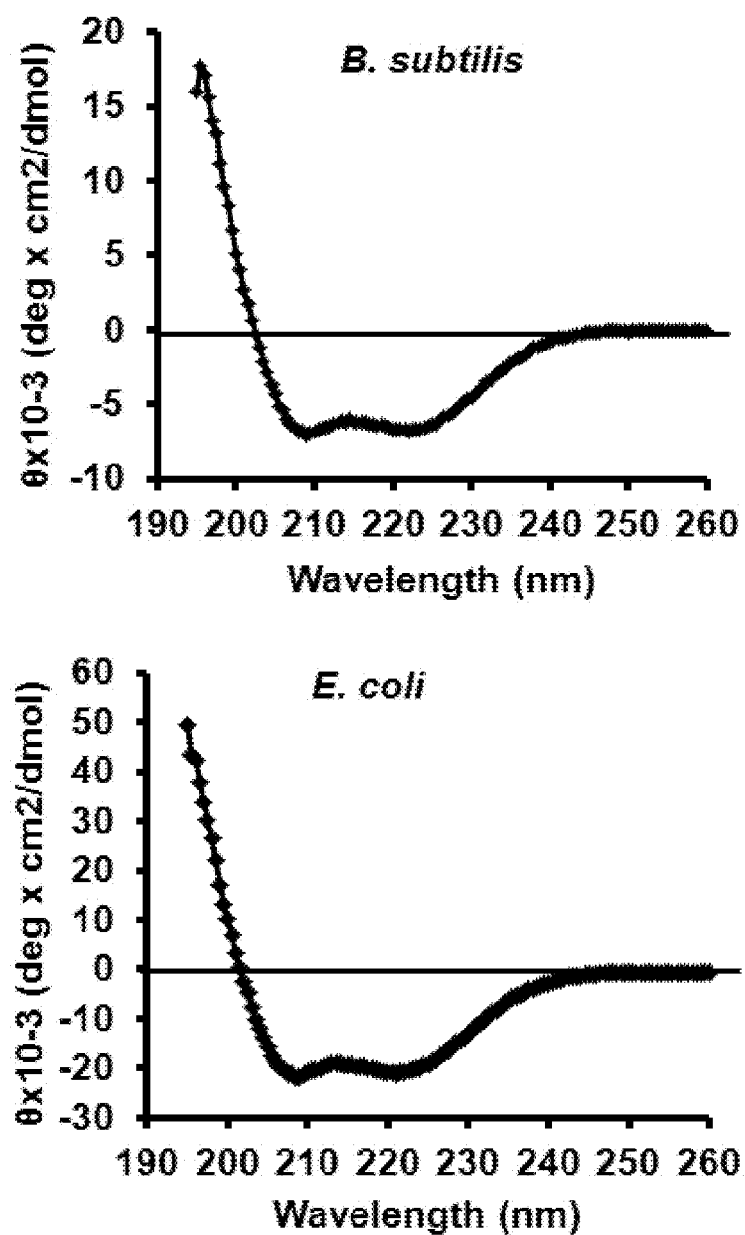
FIG. 15 exhibits the physical analysis of purified HP-NAP expressed in *B. subtilis* and *E. coli* by DEAE SEPHADEX ion exchange resins for its secondary structure.

Multimeric Structure with α-Helix of HP-NAP Purified from B. subtilis and E. coli To further determine whether the recombinant HP-NAP purified from B. subtilis and E. coli folded into its native structure, several molecular properties of the purified HP-NAP were examined. By gel filtration analysis, purified recombinant HP-NAP was eluted as a single peak with a molecular weight of about 150 kDa in the chromatogram (FIG. 13), which is consistent with previous reports (Wang et al., 2008). The sedimentation analysis further showed that the recombinant HP-NAP purified form B. subtilis and E. coli sedimented as a major peak at 9.53 S and 9.95 S, respectively, which was calculated to the molecular weight of approximate 200 kDa (FIG. 14). This calculative molecular weight of HP-NAP is very close to its theoretical molecular weight of 203 kDa, suggesting that the purified HP-NAP formed a dodecameric protein. The secondary structure of purified HP-NAP was further determined by circular dichroism (CD) spectroscopy. The far UV trace showed a curve with characteristic of an α-helix (FIG. 15). The structural and molecular properties of HP-NAP obtained in this study are similar to those shown in other reports (Table 3). Thus, the recombinant HP-NAP purified from B. subtilis and E. coli was folded in its native form as a multimeric protein with a secondary structure of α-helix.

TABLE 3

Comparison of the molecular properties of HP-NAP characterized from this and other studies.

| SDS-PAGE (kDa)[a] | Gel filtration (kDa)[a] | Sedimentation coefficient (S)/ Calculative molecular weight[b] (kDa) | Secondary structure | Native-PAGE (kDa)[a] | Reference |
|---|---|---|---|---|---|
| ~17 | ~150 | 9.53/~200 | α-helix | ~232 | This study (B. subtilis) |
| ~17 | ~150 | 9.95/~200 | α-helix | ~232 | This study (E. coli) |
| N/D[c] | N/D[c] | N/D[c] | α-helix | N/D[c] | Tonello et al. |
| ~17 | ~150 | 9.38/N/D | N/D | ~232 | Wang et al. |

[a]The experimental molecular weight calculated from indicated measurements.
[b]The molecular weight calculated from sedimentation coefficient.
[c]N/D: Not determined
NOTE:
The theoretical molecular weights of HP-NAP were 16.933 kDa and 203.196 kDa for its monomer and dodecamer, respectively, which were predicted from ExPASy.

Embodiment 5

Figure 16:
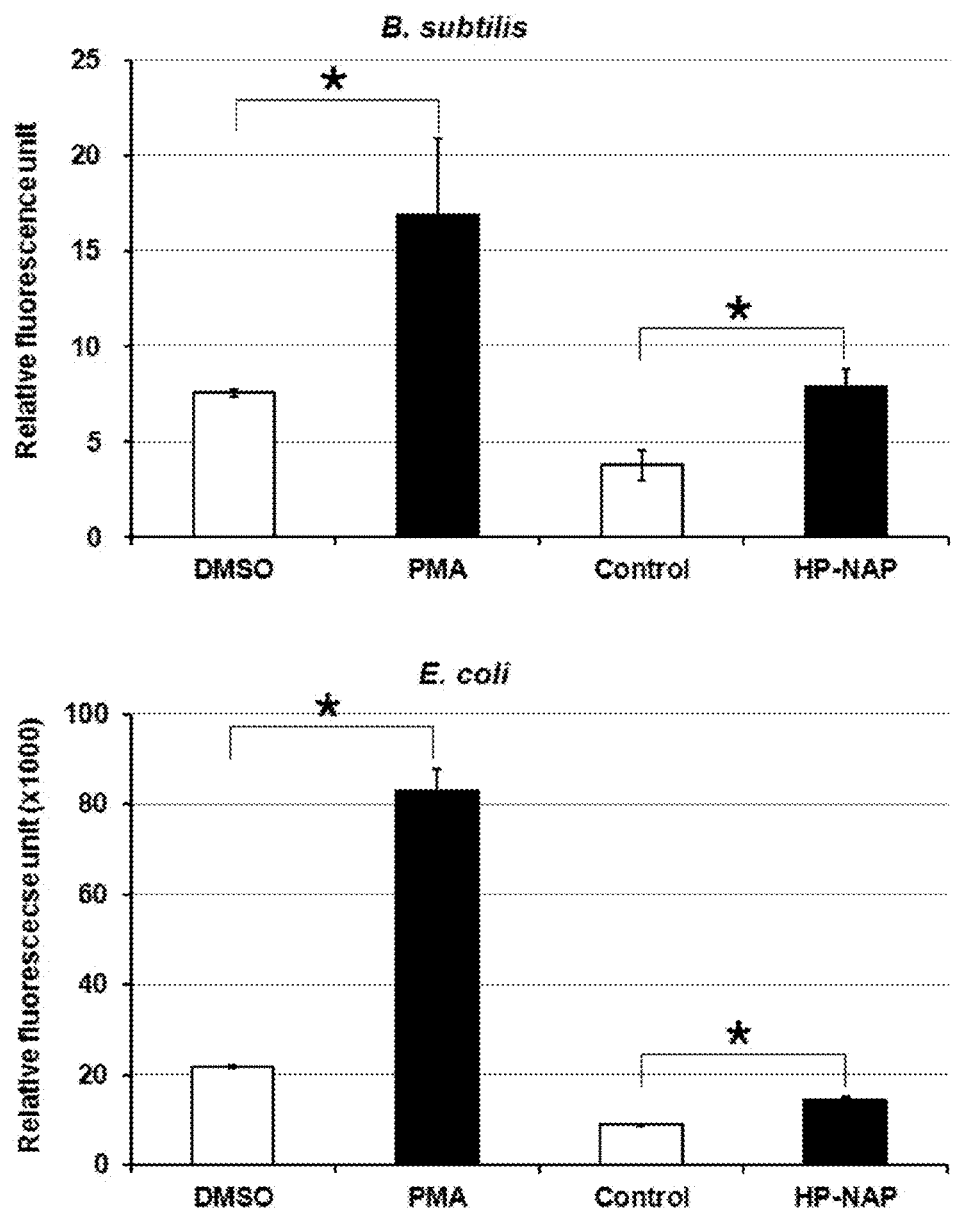
FIG. 16 exhibits ROS production of human neutrophils stimulated by recombinant HP-NAP purified from *B. subtilis* and *E. coli*.

The Recombinant HP-NAP Expressed in B. subtilis and E. coli Promotes ROS Production of Human Neutrophils After confirming physical characteristics of purified HP-NAP, whether the purified HP-NAP was biologically active can be determined by accessing its ability to induce ROS production in human neutrophils using dichlorodihydrofluorescein diacetate ($H_2$DCF-DA), a redox-sensitive fluorescent dye. HP-NAP purified from B. subtilis and E. coli induced at least a 1.6-fold increase of ROS production in the human neutrophils (FIG. 16). The results indicated that the purified HP-NAP from B. subtilis and E. coli has biological ability to stimulate the ROS production in human neutrophils.

Discussion

Figure 8:
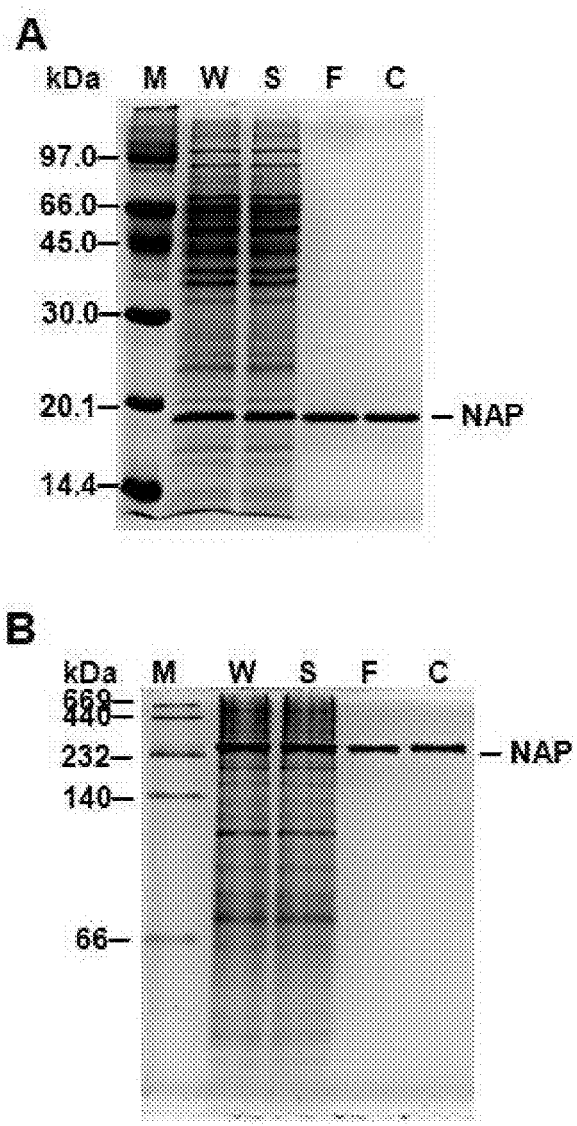
FIGS. 8A-8B exhibits purified HP-NAP expressed in *B. subtilis* by DEAE SEPHADEX ion exchange resins; 8A: soluble protein, 8B: multimeric protein.

In the present invention, B. subtilis was used as an expression system for HP-NAP production to reduce LPS contamination. The B. subtilis expression system has also been applied for the expression of recombinant HP-NAP due to the same reason in other reports (Tonello et al., 1999, Grandi, 2006). However, the purification method of HP-NAP in those reports is different from the method applied herein. In one of the reports, most of the endogenous proteins from B. subtilis were eliminated by the salting-out step with 60% ammonium sulfate, and the recombinant HP-NAP was then purified by metal chelate chromatography using the nickel chelating SEPHAROSE FF column (Grandi, 2006). The method applied herein was originally designed to apply traditional DEAE anion-exchange chromatography to purify HP-NAP according to its pI value, one will expect that pure HP-NAP could be obtained by eluting the bound HP-NAP on the DEAE resins under the pH range we investigated. Surprisingly, in the pH range between 7.5 and 9.0, HP-NAP was retained in the unbound fractions (FIGS. 4 and 5). It was rarely bound to DEAE resin at pH 8.0, and which has preferred result by using DEAE SEPHADEX (FIG. 4). Since the findings were unexpected, we designed a process of negative chromatography by using one-step DEAE SEPHADEX anion-exchange chromatography through the collection of flow-though fractions to obtain HP-NAP, of which the purity was higher than 94% (Table 1). The salt concentration in flow-though was low. Thus, it is not necessary to remove the salt from the purified HP-NAP. However, the concentration of the purified HP-NAP existed in flow-through is also low. We have used the ultrafiltration membrane with pore size of 30 kDa to concentrate HP-NAP. This step can filter proteins smaller than 30 kDa and thus achieve even higher purity of HP-NAP (FIG. 8).

In another embodiment of the present invention, the similar purification method using DEAE ion-exchange resins was applied to purify recombinant HP-NAP expressed in E. coli. In the pH range between 7.5 and 9.0, most of HP-NAP was retained in unbound and wash fractions but little of HP-NAP was bound to DEAE SEPHADEX and SEPHAROSE resins. HP-NAP was rarely bound to DEAE resin at pH 8.0, and which has preferred result by using DEAE SEPHADEX and SEPHAROSE resins (FIGS. 9 and 10). The purity of HP-NAP was raised by more than 90% through the collection of the unbound and wash fractions at pH 7.5 to 9.0. This result was similar to recombinant HP-NAP expressed in B. subtilis purified by the same range of pH values. When a process of negative purification using DEAE SEPHADEX anion-exchange resin by batch method was designed to purify HP-NAP from E. coli expression system, we have obtained recombinant HP-NAP with purity higher than 90% in one step (Table 2). Due to the high level of recombinant HP-NAP expressed in E. coli as compared to that in B. subtilis, the step of concentration is not necessary. If there is no need for buffer exchange, the step of dialysis can also be omitted to shorten the time for the purification process.

Although the present invention is described with reference to the preferred embodiments thereof, it is apparent to those skilled in the art that a variety of modifications and changes may be made without departing from the scope of the present invention which is intended to be defined by the appended claims.

REFERENCES

Grandi, G (2006) Enrichment Process for *H. pylori* Neutrophil Activating Protein (NAP) Utilizing Metal Chelate Chromatography. Italy, Chiron SRL. U.S. Pat. No. 7,038,012: 1-21.

Kawamura F and Doi R H (1984) Construction of a *Bacillus subtilis* double mutant deficient in extracellular alkaline and neutral proteases. *J. Bacteriol.* 160: 442-444.

Tonello F, Dundon W G, Satin B, Molinari M, Tognon G, Grandi G, Del Giudice G, Rappuoli R, and Montecucco C (1999) The *Helicobacter pylori* neutrophil-activating protein is an iron-binding protein with dodecameric structure. *Mol. Microbiol.* 34, 238-246.

Wang C A, Liu Y C, Du S Y, Lin C W, and Fu H W (2008) *Helicobacter pylori* neutrophil-activating protein promotes myeloperoxidase release from human neutrophils. *Biochem Biophys Res Commun.* 377, 52-56.

Yeh C. M., Wang J. P., and Su F. S. (2005) Improved electrotransformation protocol for *Bacillus subtilis* DB104. *Taiwanese J Agri Chem Food Sci,* 43, 368-375.

Yeh, C. M., Su, F. S., Wang, J. P., Liao, Y. Y. and Tsai, Y C. (2007) Enhancement of recombinant subtilisin YaB production by *Bacillus subtilis. Food Biotechnol.* 21, 105-117.

What is claimed is:

1. A method for diethylaminoethyl (DEAE) chromatography purification of recombinant *Helicobacter pylori* neutrophil-activating protein (HP-NAP), consisting the steps of:
   providing a sample containing recombinant HP-NAP without precipitating in ammonium sulfate, wherein the sample is obtained from a protein expression system that can express recombinant HP-NAP;
   purifying the sample by passing through one DEAE resin one time between range pH 8 and pH 9; and
   collecting a unbound fraction and a wash fraction obtained through above step, wherein the unbound fraction and the wash fraction contain the recombinant HP-NAP having a purity of at least 90% without passing through another resin.

2. The method as claimed in claim 1, wherein the recombinant HP-NAP is in a native form.

3. The method as claimed in claim 1, wherein the recombinant HP-NAP is a multimeric protein formed by α-helix monomers.

4. The method as claimed in claim 1, wherein the protein expression system is *Bacillus subtilis* expression system.

5. The method as claimed in claim 1, wherein the protein expression system is *Escherichia coli* expression system.

* * * * *